(12) United States Patent
Chen et al.

(10) Patent No.: US 7,390,304 B2
(45) Date of Patent: Jun. 24, 2008

(54) RESPIRATORY EXCHANGE RATIO SENSOR

(75) Inventors: Yu Chen, Shoreview, MN (US); C. Peter Howard, Humboldt, TN (US); Michael G. Snow, White Bear Lake, MN (US)

(73) Assignee: Medical Graphics Corporation, St. Paul, MN (US)

( * ) Notice: Subject to any disclaimer, the term of this patent is extended or adjusted under 35 U.S.C. 154(b) by 700 days.

(21) Appl. No.: 11/095,271

(22) Filed: Mar. 31, 2005

(65) Prior Publication Data

US 2006/0229526 A1    Oct. 12, 2006

(51) Int. Cl.
*A61B 5/083*  (2006.01)
*A61B 5/00*   (2006.01)
*A61B 5/02*   (2006.01)
*A61B 5/05*   (2006.01)

(52) U.S. Cl. .................. 600/532; 600/300; 600/484; 600/537

(58) Field of Classification Search .................. 600/532
See application file for complete search history.

(56) References Cited

U.S. PATENT DOCUMENTS

| | | |
|---|---|---|
| 4,462,764 A | 7/1984 | Van Zandt |
| 5,060,656 A | 10/1991 | Howard |
| 5,117,674 A | 6/1992 | Howard |
| 5,297,558 A | 3/1994 | Acorn et al. |
| 6,554,776 B1 | 4/2003 | Snow et al. |
| 2007/0225612 A1* | 9/2007 | Mace et al. ................. 600/532 |

OTHER PUBLICATIONS

"Hydration of Nafion Studied by AFM and X-ray Scattering", Journal of Materials Science 35 (2000) pp. 5111-5119.
Molecular Expressions: Electricity and Magnetism: Zinc-Air Battery:, Jul. 20, 2001, Interactive Java Tutorials. (6 pp).

* cited by examiner

*Primary Examiner*—Robert L. Nasser, Jr.
*Assistant Examiner*—Christian Y Jang
(74) *Attorney, Agent, or Firm*—Thomas J. Nikolai; Nikolai & Mersereau, P.A.

(57) ABSTRACT

A device for directly measuring a person's respiratory exchange ratio (RER) utilizes a Zn-air battery cell and a constant current load circuit as an $O_2$ pump capable of drawing oxygen from expired air. A thermistor located in the flow path forms a leg of a bridge circuit whose output is proportional to oxygen concentration in the expired air and, therefore, to oxygen uptake. The thermistor flowmeter circuit utilizes the thermal conductivity differences between $O_2$ and $CO_2$ to provide a measure at the relative ratio of the two gases present.

23 Claims, 7 Drawing Sheets

RESPIRATORY EXCHANGE RATIO SENSOR

BACKGROUND OF THE INVENTION

I. Field of the Invention

This invention relates generally to an apparatus and method for determining an appropriate, individualized exercise regimen to optimize the desired goal of reducing fat or improving cardiovascular performance, and more particularly to a method and apparatus for providing real-time monitoring to assist a subject in matching his/her goal.

II. Discussion of the Prior Art

As described in the Snow et al. U.S. Pat. No. 6,554,776, which is assigned to the applicants' assignee and the contents of which are hereby incorporated by reference, it is well recognized that with increasing exercise, muscles need to burn metabolic substrates to perform mechanical work. Carbohydrates and fat are then typical fuel sources that must be metabolized to provide energy. As a result of this metabolism, oxygen is consumed to provide energy and carbon dioxide is produced as a byproduct. A typical response to exercise is to increase the delivery of oxygen to the working muscles by increasing blood flow that also facilitates the removal of carbon dioxide by delivery to the lungs for excretion. This oxidative process, known as aerobic metabolism, causes a proportional increase in oxygen consumption and carbon dioxide production that is closely coupled with the level of work being performed. Aerobic metabolism uses a mixture of fat and carbohydrate substrates. The respiratory exchange ratio (RER), also sometimes called the respiratory quotient (RQ), represents the amount of carbon dioxide ($CO_2$) produced, divided by the amount of oxygen consumed ($VO_2$). At rest, and with light exercise, the RER generally ranges from 0.7 to 0.85 and is dependent, in part, on the predominant fuel used for cellular metabolism.

As the level of work continues to increase, and the ability to increase the delivery of oxygen to working muscles approaches its maximal limits, alternative methods are activated to supplement the energy produced through aerobic processes. This alternate method, known as anaerobic metabolism, predominantly uses carbohydrate substrates that disproportionately increase carbon dioxide production relative to oxygen consumption. This disproportionate increase is reflected by an increase in the RER from 0.9 to 1.3 or greater.

One of the values of the RER measurement is that it permits identification of the anaerobic threshold (AT) and, therefore, identifies the work rate where aerobic processes are no longer adequate. The term "anaerobic threshold" is based on the hypothesis that at a given workrate, the oxygen supplied to exercising muscles does not meet the oxygen requirements. This imbalance increases anaerobic glycolsis for energy generation, yielding lactate as a metabolic byproduct. The AT is a point during exercise at which ventilation abruptly increases despite linear increases in work rate and oxygen uptake. As described in the Acorn et al. U.S. Pat. No. 5,297,558, exercise prescriptions and protocols for increasing fitness and weight loss are based on knowing or assuming this threshold. Typically, the measurement is made during a baseline test and the exercise prescription is based on the threshold as determined from the RER. However, it is understood that the anaerobic threshold will change during the training period as the cardio respiratory system becomes more efficient and subsequent testing is required to adjust the prescription for the training effect.

In the past, measurement of RER has typically been possible only in laboratory environments using computerized exercise testing systems, such as that described in the Anderson et al. U.S. Pat. No. 4,462,764 and the Howard et al. U.S. Pat. Nos. 5,060,656 and 5,117,674. These devices measure ventilation using airflow, oxygen and carbon dioxide levels using discrete analyzers and a computer is employed to perform computations to determine the oxygen uptake and the carbon dioxide production. The calculation of RER is a secondary calculation. The drawback to this approach for measuring RER is the expense and complexity of integrating three sensors with a computer, aligning the signals time wise and maintaining calibration for all three sensors. The technique of ventilatory gas measurement has a number of potential limitations that hinder its broad applicability. Gas exchange measurement systems are costly and require meticulous maintenance and calibration for optimal use. Personnel who administer tests and interpret results must be trained and proficient in this technique. Finally, the test requires additional cost and time, as well as patient cooperation. Thus, a need exists for a simple, inexpensive sensor or monitor that can be directly employed by an untrained subject during the course of exercise to monitor his/her own RER. In turn, the subject may determine his/her heart rate at a detected AT and then pace his/her exercise by maintaining a heart rate at a predetermined percentage below heart rate at AT if the goal is to burn fat or at a predetermined percentage above heart rate at AT if the goal is improved cardiovascular performance.

SUMMARY OF THE INVENTION

In accordance with the present invention, the device for directing measuring a person's RER comprises a tubular housing having a lumen extending therethrough through which inspired and expired air is adapted to flow. Located in the lumen is an oxygen fuel cell battery such as a Zn-air battery that has its air inlet port facing a source of the expired air. Coupled to the Zn-air battery is a constant current load circuit. Completing the assembly is a thermistor flowmeter circuit that has a thermistor element located in the lumen of the tubular housing at a location that is between the source of expired air and the air inlet port of the Zn-air battery. The thermistor flowmeter circuit is operative to produce an output signal that is proportional to a relative ratio of carbon dioxide to oxygen present in air expired by the subject. Also located in a path between the expired air inlet and the thermistor element is a tube of a synthetic ionomer that exhibits selective permeability to water. In this way, water vapor is removed from the airstream reaching the thermistor and the Zn-air cell. Further, a heater element may be included in the sensor housing to maintain the ambient temperature at a predetermined value in the absence of expired air flowing through the tubular housing and impinging on the thermistor element.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

The present invention provides a system for measuring a subject's RER directly by monitoring relative changes in oxygen and carbon dioxide using a single sensor that produces an output signal proportional to RER. A Zn-air battery and a thermistor are employed in a novel combination to form a self-regulating system that has significant benefits, including an extremely small sensor size, low material cost, elimination of calibration procedures, and common-mode error cancellation.

A zinc/air battery consumes oxygen to provide power and is considered to be an oxygen fuel cell battery. When the load across such a battery is sufficiently high, it causes the collapse of the battery's voltage, which is nominally 1.4 volts. At 0.15 volts and less, electron conductivity exceeds ionic conductivity as the load across the battery causes the internal resistance of the battery to fall below the load resistance, resulting in the breakdown of the internal conductivity. The excess current causes hydrogen gas to be produced at the cathode in proportion to the oxygen reduction deficit via the constant current demand of the battery. Therefore, the oxygen deficiency is actually measured as hydrogen release, which has manifested itself as looking like flow. The greater the oxygen deficiency, i.e., the more the oxygen level falls below its concentration level in ambient air, the greater the amount of hydrogen produced.

Hydrogen is a gas of very high thermal conductivity and acts in total opposition to that of carbon dioxide conductivity on the thermistor. This results in a measurement of oxygen deficit or consumption in opposition to the carbon dioxide production. This secondary effect does not detract from the intrinsic performance of the device, although it calls for some engineering creativity to prevent hydrogen from building up and swamping the carbon dioxide signal. Allowing the hydrogen to escape in the expired gas stream in an orderly manner provides the linearity of signal needed for accurate analysis.

Initially, the cell is operated under steady state conditions, with $O_2$ and $CO_2$ concentrations equal to those found in room air. That is, the concentration of $O_2$ in room air is about 21% while the concentration of $CO_2$ in room air is about 0.03%. Under these conditions, the Zn-air cell produces a steady current, as long as $O_2$ is readily available. However, if the oxygen concentration decreases, the existing current will be unsustainable without an influx of oxygen. The only way to fulfill these conditions is to add more $O_2$ to the system. In this way, the cell is forced to act as an "oxygen pump" or regulator for itself. Whenever the cell lacks enough $O_2$, it must regulate its own flow and start to draw a small flow of $O_2$ into it. This flow is proportional to the oxygen concentration available.

The second part of the sensor system of the present invention is a thermistor circuit used to measure flow. The thermistor measures both oxygen flow and the inverse effect of carbon dioxide. In reality, the actual flow of oxygen at 4 milliamps is in the order of 0.1-0.2 mls/min. This flow is below the detectable limit of the thermistor, but a secondary effect allows one to measure the flow. When the zinc/air battery is subjected to current draw in excess of its rated capacity, the battery voltage falls and the device becomes polarized. It is in this state that "pumping" occurs. When an electrochemical device is polarized in this way, there is an excess of hydrogen ions at the cathode to perform the oxygen reduction. The amount of hydrogen excess is proportional to the oxygen consumption of the battery. When the oxygen partial pressure falls to below that of air, as in the case of respiratory analysis, the increase in apparent oxygen flow is caused by further release of one or more hydrogen to satisfy the constant current demand on the device. In other words, the battery becomes more polarized. Therefore, the hydrogen given off is proportional to the oxygen consumption of the battery. Hydrogen has a thermal conductivity approximately seven times that of oxygen and is easily detected by the thermistor. If the flow over the thermistor is channeled such that the hydrogen, once released from the battery, can flow over the thermistor and out of measurement system without facing a varying restriction, then the thermistor output is stable with changes of oxygen. The importance of a free path for the flow to occur is very necessary to accurate analysis. Changes in back pressure can cause a build-up of the hydrogen gas when the pressure increases or a reduction in hydrogen at lower pressures. When this happens, the hydrogen concentration is no longer proportional to the oxygen flow, which is still constant for a given oxygen level. Measuring flow accurately is the key to obtaining valid measurements for this system. The thermistor is placed directly in the air flow path entering the cell and, as such, even minute changes in flow will be sensed. When there is no flow through the sensor, heat is lost through the thermal conductivity of the gas mixture surrounding the thermistor, in this case, ambient air. This gas mixture, in turn, passes heat to the wall of the housing surrounding the thermistor. This results in the equilibrium and is the zero condition. Oxygen and nitrogen, the main components of air, have virtually identical thermal conductivities so the thermistor is unable to differentiate between $O_2$ and $N_2$.

As the oxygen concentration in the exhaled breath becomes lower than 20.9%, which is the amount of $O_2$ normally in air, the demand for more oxygen flow by the Zn-air cell, running at a constant current, increases to compensate for the lower oxygen partial pressure. The lower the oxygen concentration, the higher the flow.

Other components of exhaled breath are $CO_2$ and water vapor. These have thermal conductivities different from air, with $CO_2$ being lower and water vapor being higher. As exhaled breath contains water vapor, it is necessary to equilibrate the water vapor in the breath with ambient air. Water vapor has a higher thermal conductivity and would cause an increase in apparent flow. The water vapor constituent is equilibrated by passing the sampled gas through a tube of a synthetic ionomer that exhibits selective permeability to water. NAFION® tubing is such an ionomer. By passing the sampled gas through the NAFION tube, excess water vapor in the sample is reduced to that of the ambient air.

$CO_2$, also present in the exhaled breath, reduces the apparent flow because its thermal conductivity is lower than that of air. Taking advantage of this characteristic is a key aspect of the present invention. In an ideal situation, if every volume of $CO_2$ produced was equal to every volume of oxygen consumed, there would be no change of flow and this would represent an RER of 1.0. However, the "Carrier Gas" effect of $CO_2$ must be taken into account. This effect is a function of the viscosity change in the exhaled gas due to $CO_2$. $CO_2$ being a very viscous gas promotes easier passage of oxygen to the Zn-air cell, thus reducing the flow effect due to oxygen demand. Therefore, at high RER numbers, where the $CO_2$ concentrations are large, there is a roll off of flow with marked decrease in the linearity of signal above an RER of 1.0.

As the temperature of the air flowing past the thermistor changes, so does the resistance of the thermistor. The changing resistance of the thermistor is measured precisely by a bridge circuit. The loss of power due to flow over the thermistor is compensated by the Wheatstone bridge. The resulting output voltage can be characterized by the following equation that relates the voltage across the thermistor to the rate of flow:

$$v \sim ((e^2 * \Delta T)/R_s)^{1.87},$$

where $v$ is the flow rate, $e$ is the voltage across the thermistor, $R_s$ is the resistance of the thermistor as measured by the Wheatstone bridge, and $\Delta T$ is the temperature gradient caused by the air flow.

This air flow, then, is the same flow that interacts with the Zn-air cell. $CO_2$ and $O_2$ compose the main gases present in this air flow. Both gases differ in thermal conductivity, or the intrinsic rate of heat loss. $CO_2$ has a much lower thermal conductivity, approximately 0.017 W/mK, than does $O_2$ with 0.027 W/mK. The thermistor flowmeter circuit utilizes the thermal conductivity differences between the flow due to $O_2$ and $CO_2$ to provide a measure of the relative ratio of the two gases present. In other words, the voltage quantity in the above equation is actually indicative of the relative amount of power required to make up the heat loss caused by the gas flow. When $CO_2$ passes over the thermistor, it acts like a blanket and the heat loss slows down, resulting in a net effect of reducing the flow output. Combining the $O_2$ and $CO_2$ effect on the flow rate results in a superposition of flow past the thermistor. Consequently, differences in thermal conductivity produce differences in flow rate. A significant benefit is the reduction of the common mode error present in the flow measurement. By using the Zn-air cell to regulate flow, the thermistor to measure the resulting flow into the cell, a total flow rate is obtained which is proportional RER measurement.

Having described the underlying theory of operation of the RER sensor of the present invention, attention will next be directed to the mechanical and electrical construction of a prototype sensor for monitoring RER.

Figure 1:
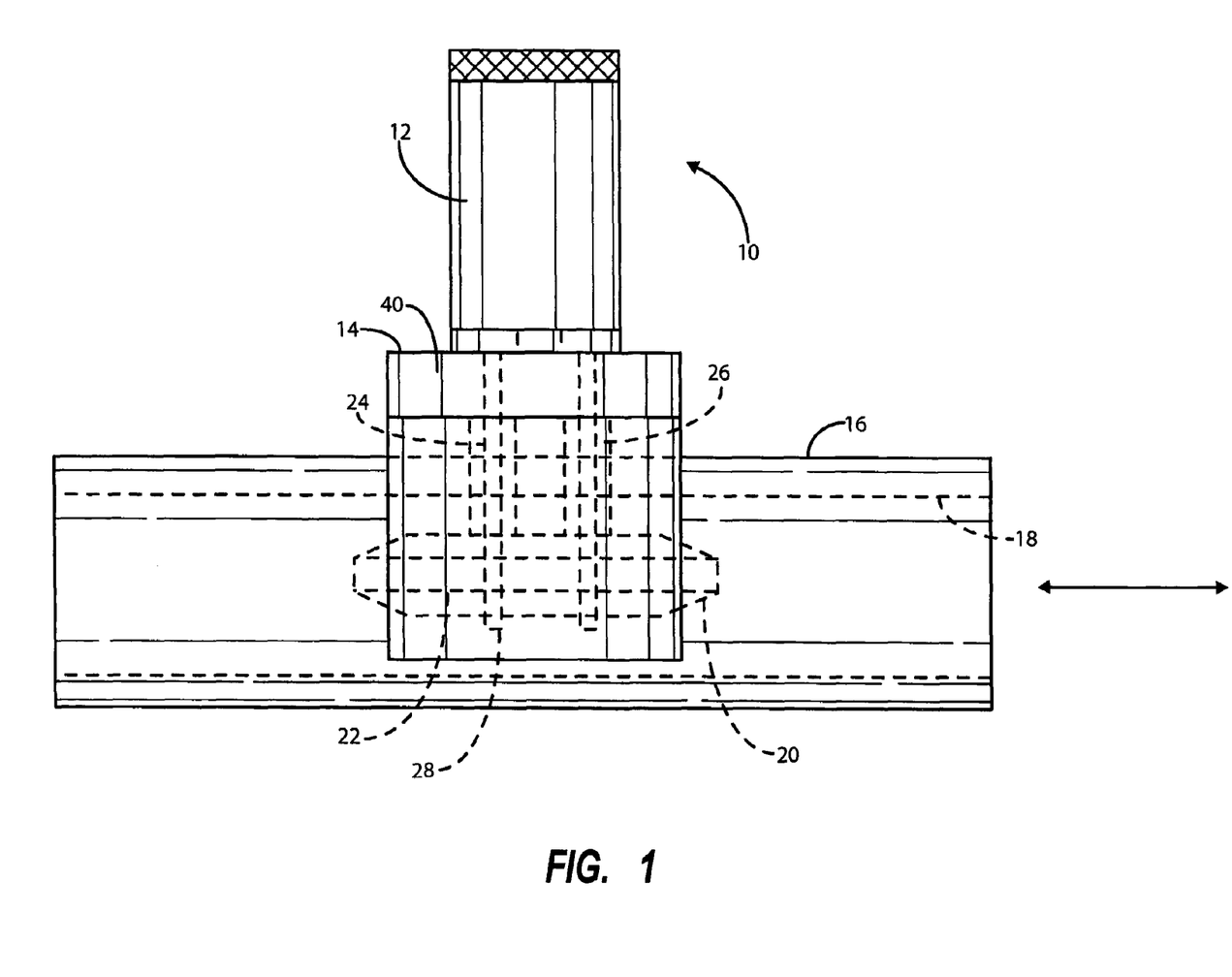
FIG. 1 is a side elevational view of a mouthpiece with the RER sensor of the present invention mounted thereon.

Referring to FIG. 1, there is indicated generally by numeral 10 a sensor module comprising a cylindrical, tubular shell 12 that is affixed to a mounting saddle 14. The mounting saddle surrounds and is clamped to a tubular mouthpiece 16. The mouthpiece 16 has a central lumen 18 and is preferably made from a suitable plastic, such as an acrylic. The outside diameter of the mouthpiece 16 is such that it can comfortably fit within the mouth of a subject and held there by the subject's lips during a phase of an exercise regimen in which that subject's RER is to be monitored. Concentrically disposed within the lumen 18 of the mouthpiece member 16 is a sampling tube 20 having a series of internal passages for directing inspired and expired air to and from the sensor module 10. The sampling tube 20 is maintained in a centered relation within the lumen 18 of the mouthpiece 16 by tubular standoff spacers 24 and 26. Extending through the lumen of spacer tube 24 is a fine capillary tube 28, preferably formed from a synthetic ionomer exhibiting selective permeability to water vapor. One such material is available from the DuPont Corporation under the trademark, NAFION®.

Figure 2:
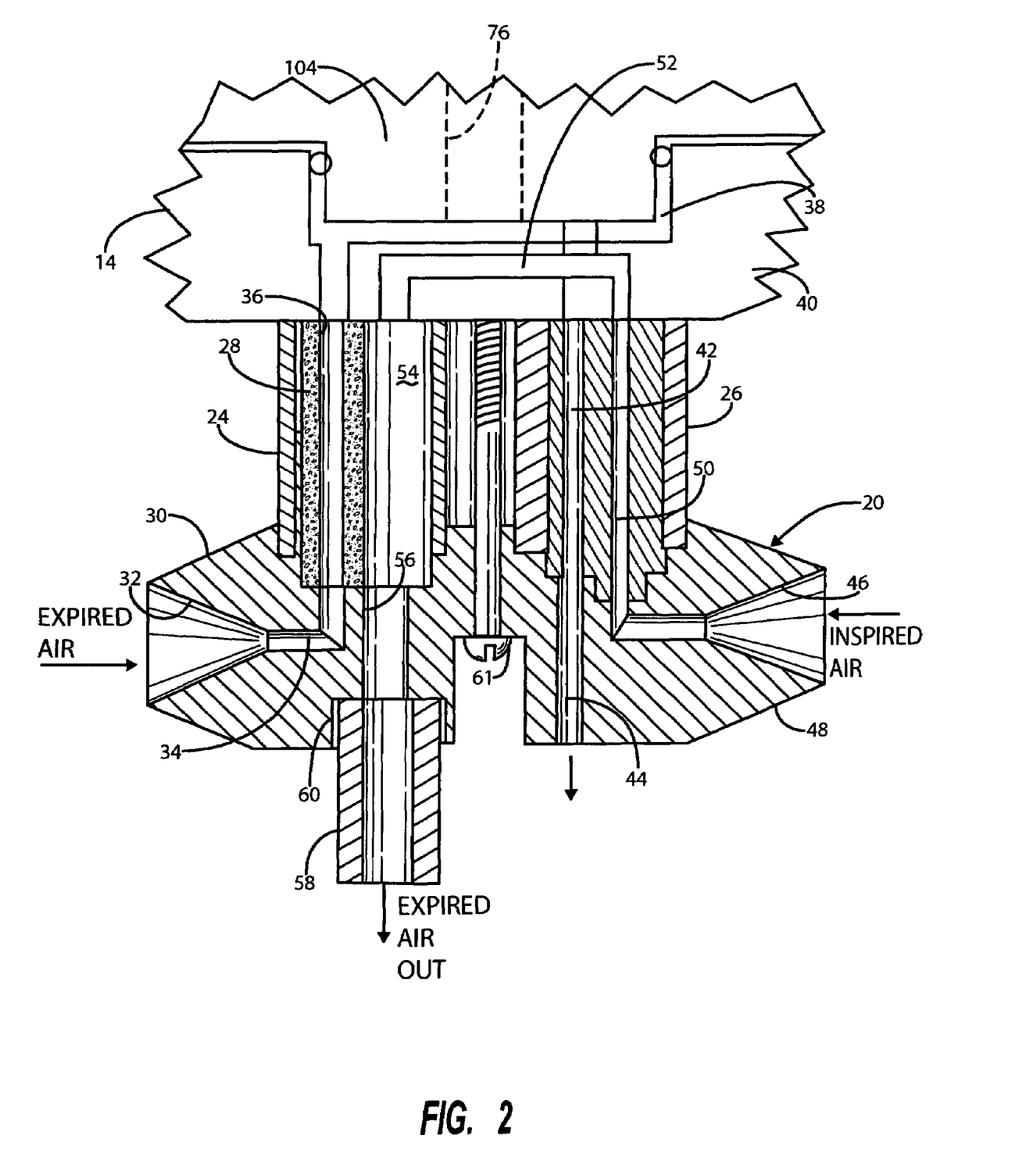
FIG. 2 is a cross-sectional view of the RER air sampling module.

The greatly enlarged cross-sectional view of FIG. 2 shows that the sampling tube 20 has a bullet-shape nose on opposed ends thereof. The nose 30 has a conically-shaped opening 32 leading to a right angled bore 34, the vertical portion of which is aligned with the lumen 36 of the NAFION tube 28 located in the lumen of the tubular strut 24. Because of the properties of the NAFION tube, moisture-ladened air expired from a subject's lungs has the moisture component thereof extracted by passing through the wall of the NAFION tube 28 and the dried air then enters a sampling chamber 38 formed in the base 40 of the mounting saddle 14. The dried expired air exits the chamber 38 by way of a bore 42 that extends through the tubular strut 26 and that is in fluid communication with a further bore 44 formed through the sample tube 20. As the subject inhales, inspired air is drawn through the conically-shaped opening 46 formed in the nose 48 and through a bore 50 formed internally of the tubular strut 26. The bore 50 is in fluid communication with a fluid pathway 52 formed in the base member 40. This pathway leads to the lumen 54 of the tubular strut 24 and picks up the moisture exiting through the walls of the NAFION tube 28, carrying that moisture through a bore 56 formed diametrically through the sampling tube 20 and out through a pitot tube 58 that is fitted into a counterbore 60 formed in the sampling tube.

The sampling tube 20 is fastened to the base 40 of the mounting saddle 14 by means of an elongated screw, as at 61, such that the tubular standoffs 24 and 26 become clamped between the sampling tube 20 and the base 40 of the mounting saddle to thereby secure the several lumens in the tubular struts in appropriate alignment with mating lumens in the sampling tube member 20.

Figure 3:
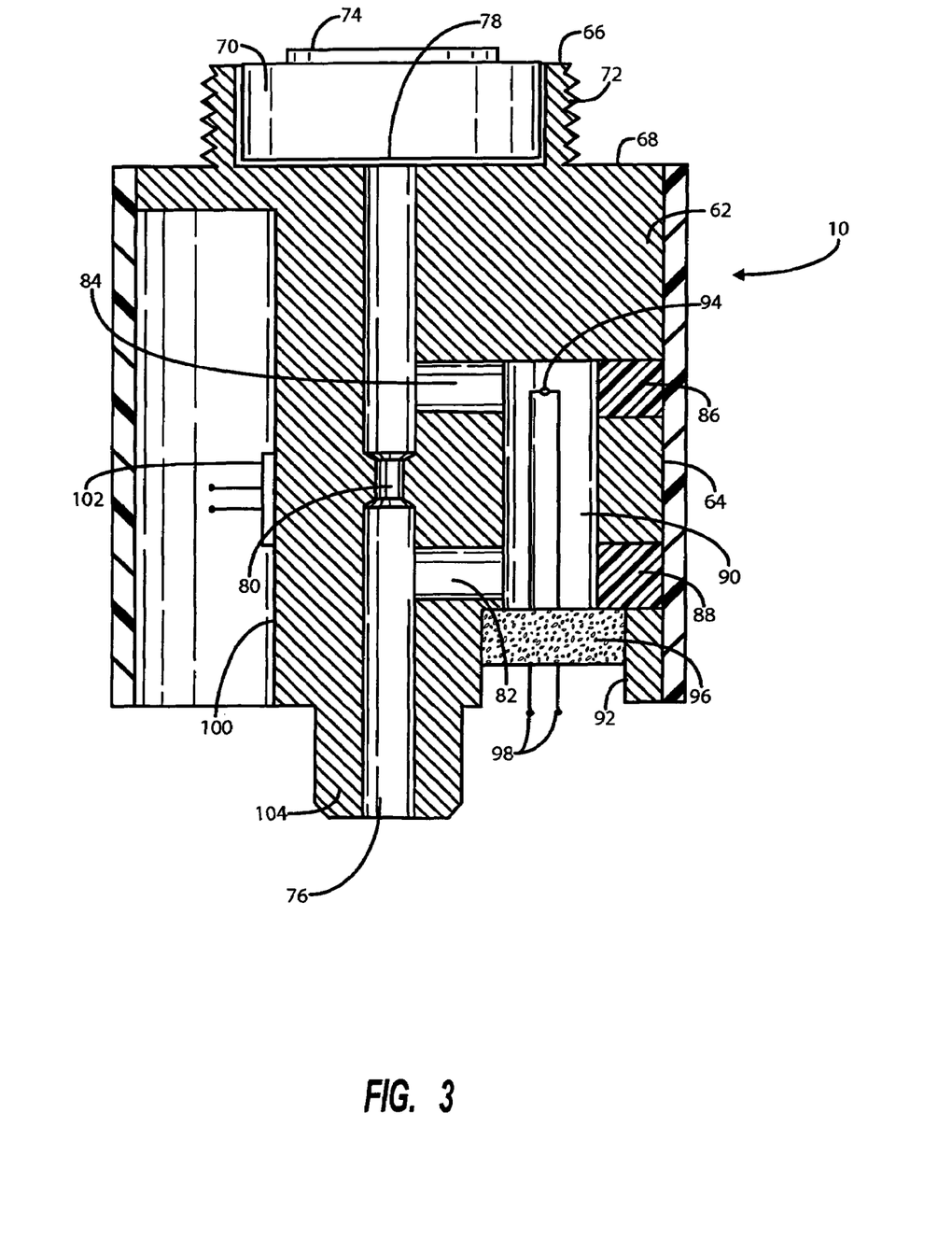
FIG. 3 is a cross-sectional view of the RER sensing device.

Turning next to FIG. 3, there is shown a greatly enlarged, cross-sectional view of the sensor module 10 comprising a preferred embodiment of the present invention. It comprises a body 62 preferably formed from a suitable metal, such as brass or aluminum and which is generally cylindrical and is contained within an insulating cover sleeve 64. An integrally formed annular hub 66 projects from the top surface 68 of the body member 62 forming a cup-like pocket dimensioned to contain a Zn-air cell 70 of a type commonly used for powering hearing aids. The annular projection 66 includes screw threads 72 on its outer diameter allowing a cap member (not shown) to be screwed onto the projection 66 for holding the cathode of the cell 70 in contact with the metal sensor body 62 and with the anode 74 of the cell in contact with a conductor connecting the cell to a constant current load circuit as will be described in greater detail herein below with the aid of FIG. 5.

A longitudinal bore 76 is aligned with an aperture 78 formed centrally in the bottom of the Zn-air cell 70. Without limitation, the bore 76 may be about 0.0052 in. in diameter over a majority of its length but narrows to about 0.025 in. midway along its length to create a choke 80. Two additional radially extending bores 82 and 84 are drilled through the side wall of the cylindrical body member 62 to intersect with the bore 76 and subsequently, the bore entrances are plugged with epoxy or other suitable material as at 86 and 88 in FIG. 3.

A further longitudinal bore 90 is formed inwardly from a bottom end of the body member 62 as is a counterbore 92. Placed within the bore 90 is a temperature sensitive resistance, such as a thermistor 94. The base 96 of the thermistor component fits into the counterbore 92 with lead terminals 98 extending outward from the sensor housing, allowing connection to the hot wire flowmeter circuit illustrated by the schematic diagram of FIG. 6.

Bonded to the surface 100 of the sensor body 62 is a resistance heater 102 and which may comprise a Type DN-505 subminiature, proportionally controlled heater whose temperature can be programmed with a single external resistor. This device is well suited for regulating the ambient temperature within the sensor module 10.

The Zn-air cell 70 has its cathode placed so that its air inlet port 78 is aligned with the lumen 76 and, as such, the air inlet port 78 of the cell is in fluid communication with expired air breathed into the mouthpiece 16 and which impinges upon the funnel-like lumen 32 of the sampling tube 20. The expired air breath then travels through the ionomer tube 28 that is selectively permeable to moisture, such that a relatively dry sample of the subject's expired air ultimately reaches the sampling chamber 38.

The prototype module constructed by applicants has been especially designed to eliminate leaks within the system. Since flow, regulated by the Zn-air cell, is extremely low (less than 100 cc/min), minimizing unintentional airflow is imperative for proper operation. The air inlet chamber through the center of the module is the only entrance for air into the system. If $O_2$ is depleted near the cell 70, then a pressure drop within the chamber defined by the bores 72, 82, 84 and 90 comprising the sensor occurs, necessarily creating a flow of $O_2$ into the Zn-air cell 70 to satisfy the constant current requirements.

Due to the presence of the choke 80 in the bore 76, oxygen being drawn by the cell 70 passes through the shunt branch and over the thermistor 94 which is configured as a component of a hot-wire flowmeter circuit.

Figure 4:
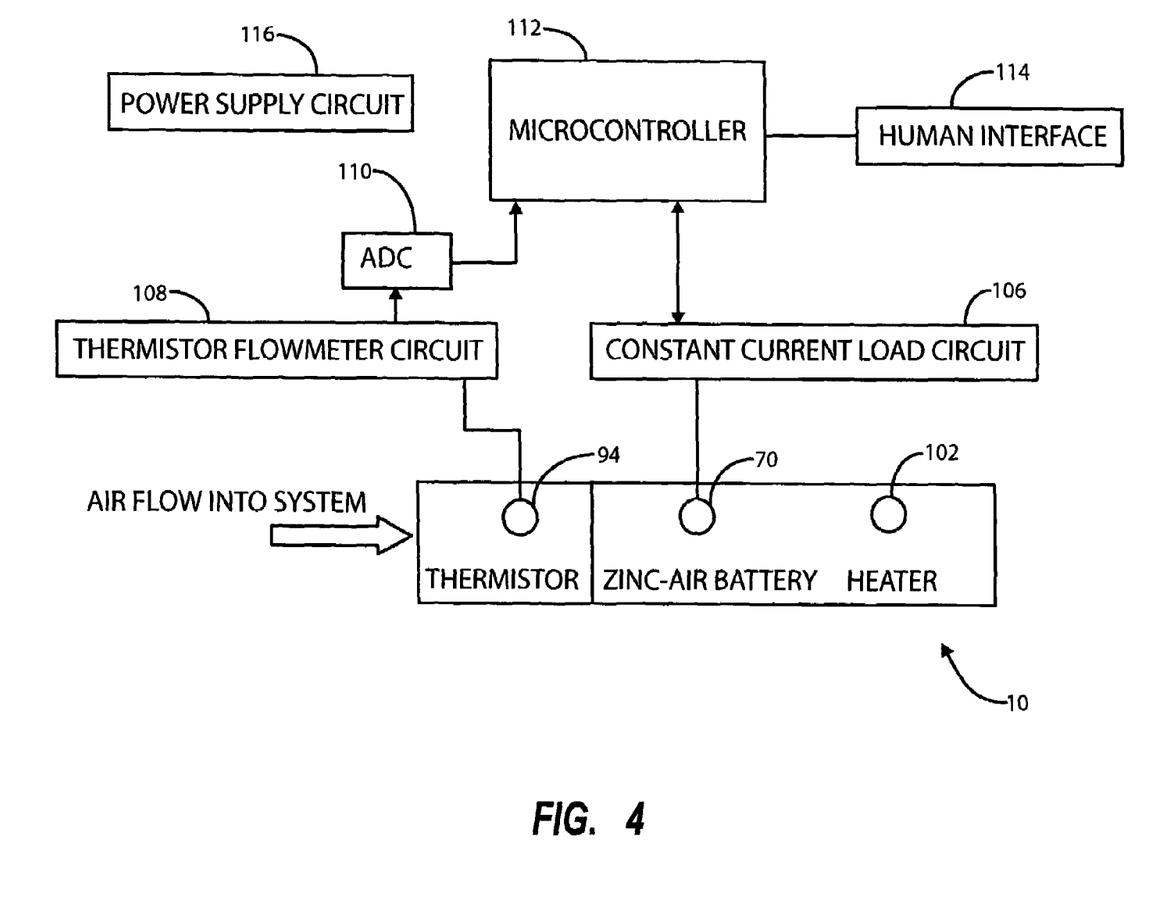
FIG. 4 is an electrical block diagram of the RER sensor assembly.

Referring next to FIG. 4, there is schematically shown an electrical block diagram of the respiratory exchange ratio monitoring device. It includes the sensor module 10, a constant current load control circuit 106 connected to the Zn-air battery 70, and a thermistor flowmeter circuit 108 connected to the thermistor bead 94. The thermistor flowmeter circuit 108 feeds an analog output signal to an analog-to-digital converter 110 whose output is then connected to a data input terminal of a microprocessor-based controller or microcontroller 112. The microcontroller 112, in turn, controls the constant current load control circuit 106 and feeds information to a human interface device 114. A power supply circuit 116 provides the necessary operating potentials to the heater element 102 located in the sensor 10 to the microcontroller 112, the analog-to-digital converter 110 and the flowmeter circuit 108. The system automatically keeps the Zn-air battery circuit current constant by feedback control and monitors output signal proportional to the RER from the thermistor flow circuit.

Figure 5:
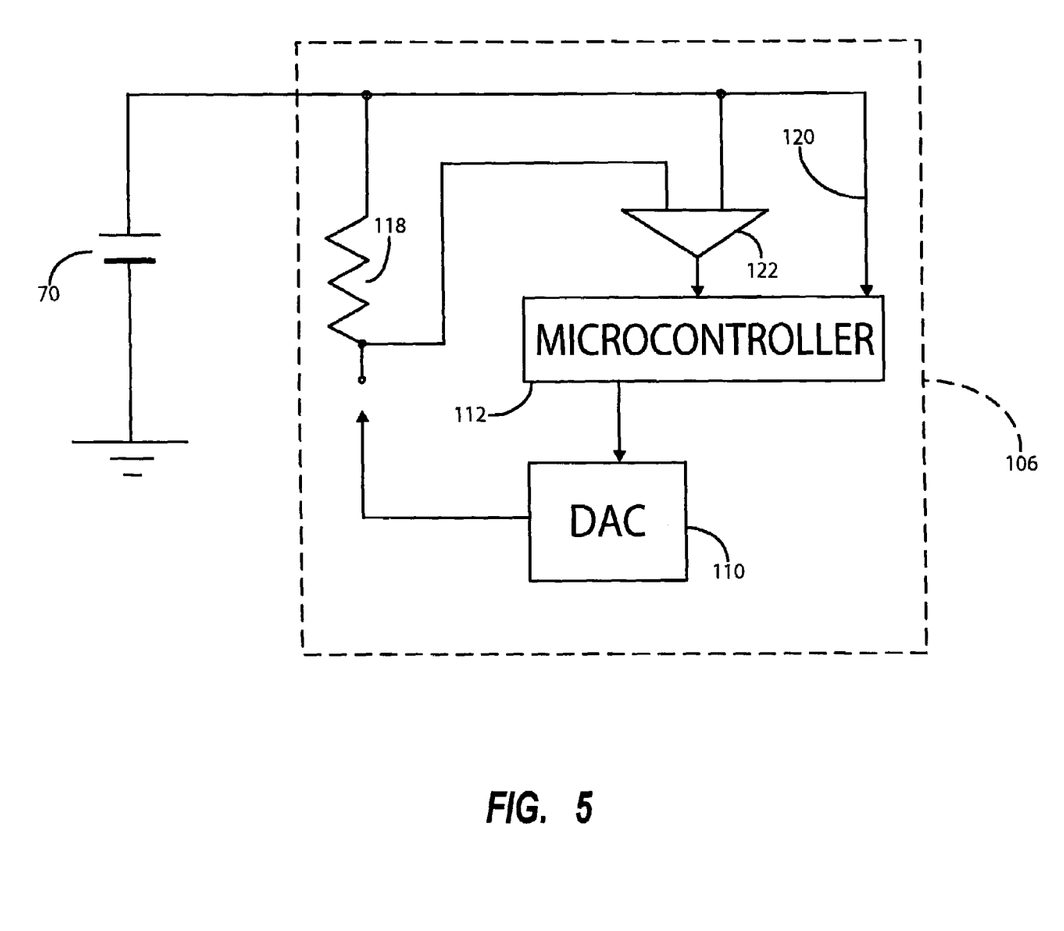
FIG. 5 illustrates the Zn-air battery coupled to a constant current load control circuit.

Referring next to FIG. 5, there is shown an electrical circuit diagram of the Zn-air battery 70 coupled to its constant current load control circuit 106 that is enclosed by a dashed line box in FIG. 5. While a particular design of a constant current load control circuit is illustrated, those skilled in the art can readily devise alternative arrangements and, hence, limitation of the invention to the one particularly illustrated in FIG. 5 is not intended. In FIG. 5, the Zn-air battery 70 is connected with a sensing resistor 118 of relatively small ohmic value, such as about 20 ohms. The output of a digital-to-analog converter 110 serves to vary the voltage drop across the sensing resistor. The microcontroller 112 monitors the cell voltage, via input 120, as well as the amplified voltage from the sensing resistor 118 and, consequently, adjusts the output of the digital-to-analog converter 110 to keep current drain from the cell constant due to the applied feedback control.

In operation, constant current flows through the sensing resistor 118 and into the output of the DAC 110. The voltage output of the DAC is adjusted dynamically by the microcontroller 112. At every 100 ms interval, the microcontroller 112 samples the cell voltage, calculates the required voltage at the DAC output and changes the DAC output correspondingly. This step may be referred to as the coarse tuning. After a 50 ms delay in which the circuit can stabilize, the microcontroller samples the amplified voltage output from amplifier 122 taken across the sensing resistor and adjusts the DAC output to compensate any difference from the ideal value. This part of the algorithm may be referred to as "fine tuning" and may be repeated at prescribed intervals. In actual testing on the prototype described, this specific coarse/fine tuning algorithm resulted in high accuracy, constant current with only about a 0.3% variance.

Figure 6:
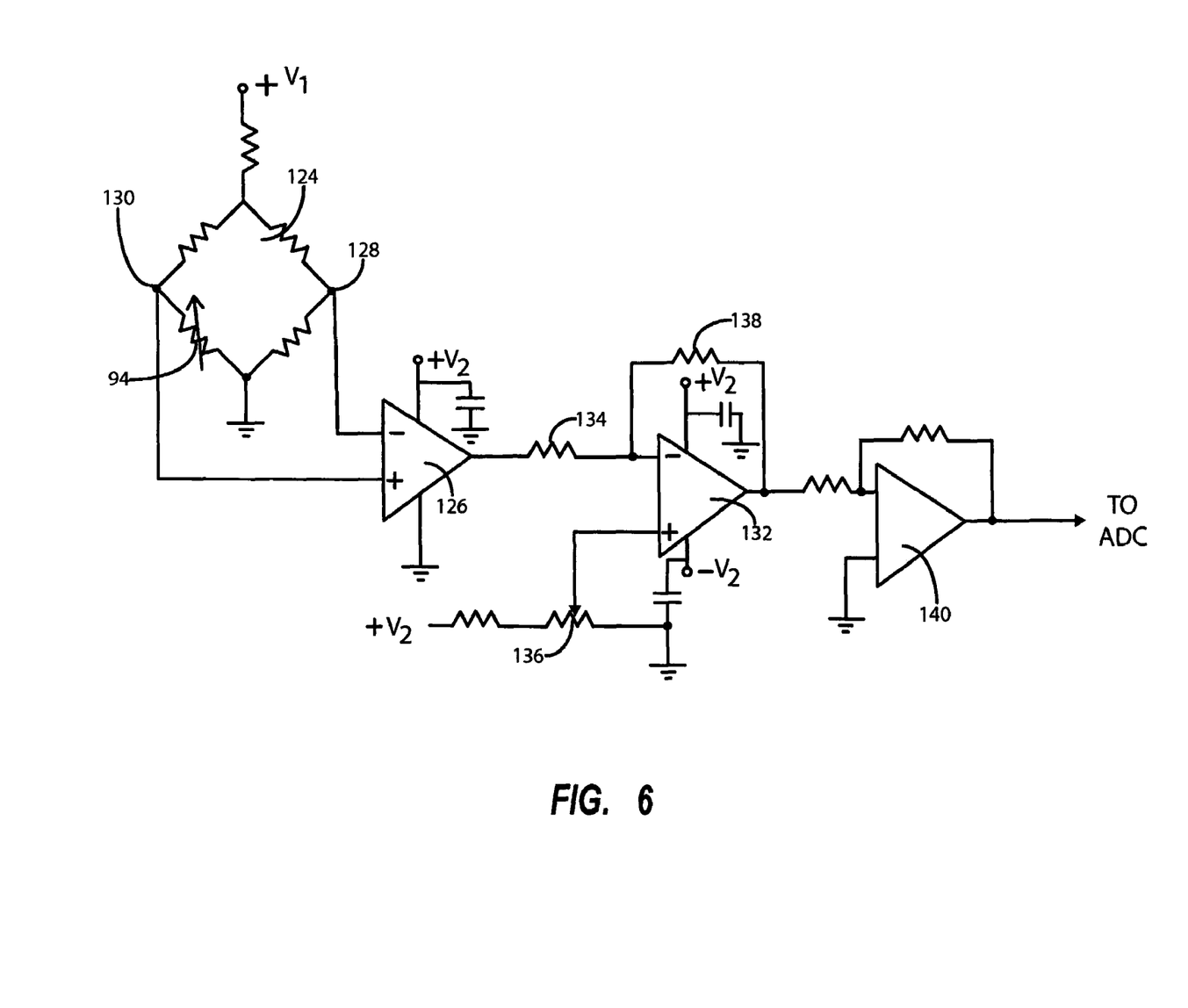
FIG. 6 is an electrical schematic diagram of the thermistor flowmeter circuit used in the assembly of FIG. 3.

FIG. 6 illustrates a schematic electrical diagram of the thermistor flow control circuit employed in the preferred embodiment. Again, persons skilled in the art can devise alternative circuit arrangements for deriving flow-related information employing a thermistor and all such circuit arrangements should be considered to be equivalent to that which is specifically disclosed herein. It includes a Wheatstone bridge 124 having the thermistor bead 94 in one arm thereof and an operational amplifier 126 connected across the output terminals 128 and 130 of the bridge.

As expired air flows over the thermistor element, its temperature changes from the ambient temperature in the body 62 maintained by the heater 102 causing the bridge to output a signal that varies with flow. The operational amplifier 126 amplifies this signal and outputs a signal to a further operational amplifier 132 through a coupling resistor 134. The positive input terminal of the operational amplifier 132 connects to the wiper arm of a potentiometer 136 allowing the reference voltage applied to the operational amplifier 132 to be adjusted. A feedback resistor 138 is connected between the output of the operational amplifier 132 and its negative input terminal. The circuit components are selected such that the operational amplifier 132 functions to remove the DC baseline from the signal coming from the sensing amplifier 126. The resulting AC components are, in turn, amplified by the operational amplifier 140 and they are digitized by an analog-to-digital converter 110, allowing the waveforms to be processed by the microprocessor in the microcontroller module 112.

The human interface 114 shown in FIG. 4 may take on various forms. Where the purpose of the present invention is to provide an indication during exercise where the anaerobic threshold is reached, the interface may comprise first and second LED indicators where the first LED indicator is illuminated below the anaerobic threshold and the second indicator is made to glow when the anaerobic threshold is exceeded. If the goal of the subject in performing exercise is to lose weight (burn fat), then the exercise level should be maintained such that heart rate is a predetermined value less than heart rate at AT. On the other hand, if the goal of the exercise is to enhance cardiorespiratory performance, then the level of exercise should be such that the heart rate at AT is exceeded. Instead of using simple indicator lamps, it is also conceived that the human interface may be aural or tactile.

Figure 7:
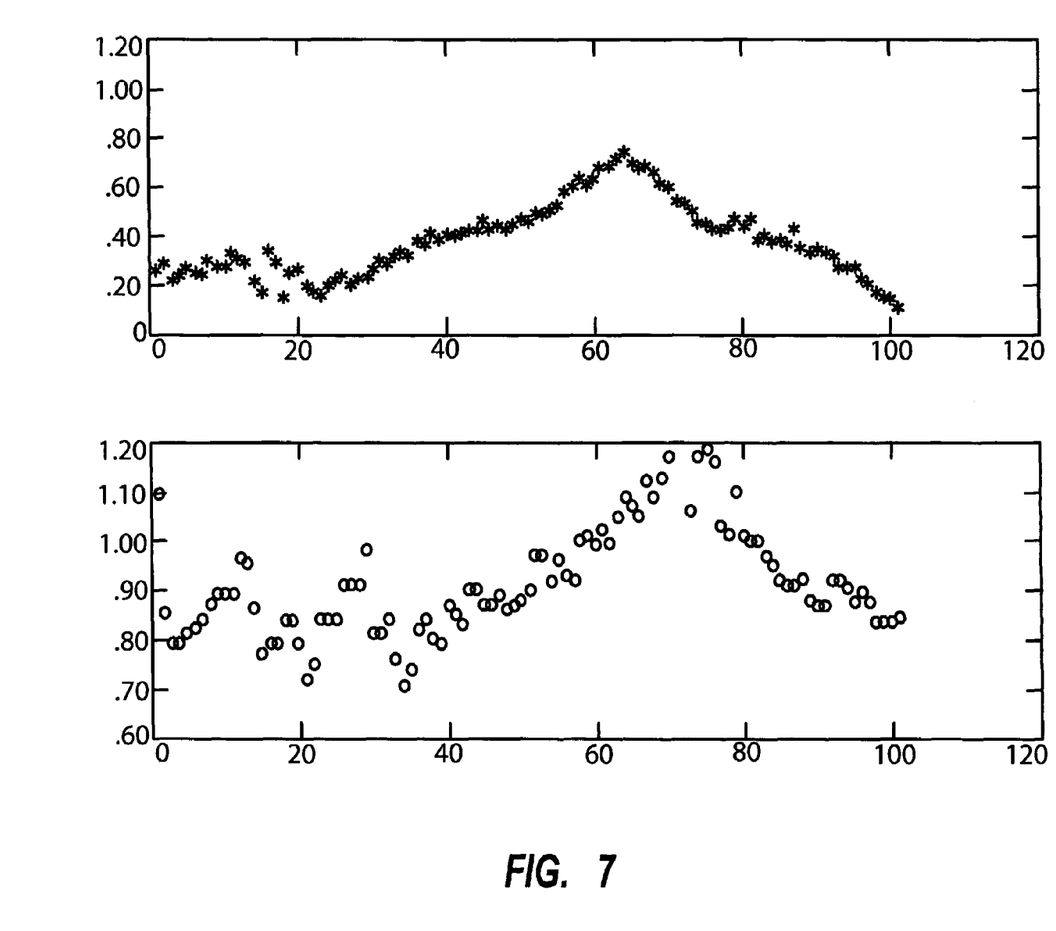
FIG. 7 are plots showing the correlation between RER as measured with the sensor of the present invention and RER measured using laboratory equipment for obtaining $O_2$ uptake and $CO_2$ production.

In FIG. 7, the upper plot shows the variation of RER when measured in a laboratory environment using a suite of equipment like that described in the aforereferenced Anderson et al. '764 patent. The lower plot shows the variation of RER with exercise when using the direct method of RER measurement obtained from a prototype of the present invention. The correlation between the two sets of data indicates that the device of the present invention can be calibrated and reliably used to measure RER.

It can be seen, then, that the present invention provides a small, portable, relatively inexpensive instrument for directly measuring a subject's RER and, therefore, a level of exercise intensity. By simply breathing through the instrument while performing exercise, an indication can be given on whether the energy substrate being consumed is primarily fat or carbohydrates.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A device for directly measuring a person's respiratory exchange ratio comprising, in combination:
   (a) a housing having a lumen extending therethrough through which inspired and expired air is adapted to flow;
   (b) an oxygen fuel cell battery positioned in said lumen with an air inlet port of said battery facing a source of the expired air;
   (c) a constant current load circuit coupled to the oxygen fuel cell battery; and
   (d) a flowmeter circuit having a sensor element disposed at a location between the source of expired air and the air inlet port of said battery, said flowmeter circuit operative to produce an output signal proportional to a relative ratio of carbon dioxide to oxygen present in air expired by the person.

2. The device of claim 1 and further including a means disposed in a flow path communicating with source of expired air for removing water vapor from the expired air impinging on said sensor element.

3. The device as in claim 2 wherein said means is a tube of a synthetic ionomer exhibiting selective permeability to water.

4. The device as in claim 1 wherein the oxygen fuel cell battery comprises a zinc/air battery.

5. The device as in claim 1 wherein the element is a thermistor.

6. The device of claim 5 and further including a heater element for maintaining the interior of said tubular housing proximate the thermistor at a predetermined ambient temperature when no expired air is impinging on the thermistor.

7. The device of claim 4 wherein the constant current load circuit includes a sensing resistor and a variable resistance connected in parallel with the zinc/air battery.

8. The device of claim 1 wherein the flowmeter circuit comprises a Wheatstone bridge circuit with a thermistor element in one leg of said Wheatstone bridge circuit.

9. The device of claim 1 and further including an indicator coupled to receive said output signal for indicating whether, during exercise, the person's ventilatory threshold is being exceeded.

10. The device of claim 5 and further including a heater element for maintaining the interior of said tubular housing proximate the thermistor at a predetermined ambient temperature when no expired air is impinging on the thermistor.

11. The device of claim 3 wherein the constant current load circuit includes a sensing resistor and a variable resistance connected in parallel with the oxygen fuel cell.

12. The device of claim 3 wherein the flowmeter circuit comprises a Wheatstone bridge circuit with a thermistor element in one leg of said Wheatstone bridge circuit.

13. The device of claim 3 and further including an indicator coupled to receive said output signal for indicating whether, during exercise, the person's ventilatory threshold is being exceeded.

14. A device for directly measuring a person's respiratory exchange ratio comprising in combination:
   (a) a tubular mouthpiece member;
   (b) a sampling tube centrally disposed in a lumen of the tubular mouthpiece member, the sampling tube having an expiratory air inlet port and an inspiratory air inlet port, an expiratory air outlet port and an inspiratory air outlet port;
   (c) an ionomer tube exhibiting a selective permeability to water vapor coupled between the expiratory air inlet port and a sample chamber for drying expired air passing through the ionomer tube to the sampling chamber;
   (d) a passageway for carrying inspired air over an exterior of the ionomer tube in traveling from the inspired air inlet port to the inspired air outlet port; and
   (e) a sensor module secured to the mouthpiece and arranged to draw oxygen from the air in said sample chamber where the flow of oxygen is proportional to the oxygen concentration of the air in the sample chamber.

15. The device as in claim 14 and further including a hot wire flow meter disposed in the sensor module and producing an electrical signal proportional to a relative ratio of $CO_2$ to $O_2$ in the air drawn from the sample chamber.

16. The device as in claim 15 wherein the hot wire flow meter includes a thermistor disposed in at least one arm of a Wheatstone bridge circuit.

17. The device as in claim 13 and further including heating means for regulating the ambient temperature within the sensor module.

18. The device as in claim 13 wherein the sensor module includes an oxygen pump for drawing the oxygen from air in the sample chamber.

19. The device as in claim 18 wherein the oxygen pump comprises a Zn-air cell coupled to a constant current load circuit.

20. The device as in claim 19 wherein the constant current load circuit includes a sensing resistor connected having a first terminal to a cathode electrode of the Zn-air cell and a second terminal connected to an adjustable voltage source; and a feedback control circuit coupled across the sensing resistor and controlling an output voltage from the adjustable voltage source.

21. The device as in claim 20 wherein the feedback control circuit comprises an operational amplifier connected to receive an input signal proportional to current flowing through the sensing resistor, a microprocessor-based controller coupled to receive an output signal from the operational amplifier; and a digital-to-analog converter connected to receive digital data from the microprocessor-based controller and applying an analog output to said second terminal of the sensing resistor.

22. A method of determining an appropriate exercise regimen for a person to optimize one of fat burning and cardiovascular performance comprising the steps of:
   (a) providing the device of claim 9;
   (b) coupling the device of claim 9 to a mouthpiece;
   (c) inserting said mouthpiece into the person's mouth;
   (d) causing the person to perform exercise at an increasing work rate;
   (e) observing said indicator and noting when the person's ventilatory threshold is reached;
   (f) measuring the heart rate of the person when the ventilatory threshold is reached; and (g) prescribing an exercise regimen wherein the level of work to be performed is such that a predetermined percentage of the measured heart rate is achieved.

23. The method of claim 22 and further including the step of advising the person to exercise at a level where the person's heart rate is below the heart rate measured when the person's ventilatory threshold is reached when fat burning is to be optimized and advising the person to exercise at a level where the person's heart rate is above the heart rate measured at the person's ventilatory threshold is reached when cardiovascular performance is to be optimized.

* * * * *